United States Patent
Svojanovksy

(10) Patent No.: US 8,600,492 B2
(45) Date of Patent: Dec. 3, 2013

(54) METHOD AND SYSTEM FOR EEG ARTIFACT CORRECTION IN COMBINED EEG AND FUNCTIONAL MRI RECORDING

(75) Inventor: Alexander Svojanovksy, Gilching (DE)

(73) Assignee: Brain Products GmbH, Gilching (DE)

( * ) Notice: Subject to any disclaimer, the term of this patent is extended or adjusted under 35 U.S.C. 154(b) by 194 days.

(21) Appl. No.: 13/017,062

(22) Filed: Jan. 31, 2011

(65) Prior Publication Data
US 2012/0197152 A1    Aug. 2, 2012

(51) Int. Cl.
*A61B 5/0476* (2006.01)
*A61B 5/0482* (2006.01)

(52) U.S. Cl.
USPC .......................................... 600/544; 600/545

(58) Field of Classification Search
USPC .................................. 600/544, 545
See application file for complete search history.

(56) References Cited

U.S. PATENT DOCUMENTS

| | | | | |
|---|---|---|---|---|
| 5,513,649 | A * | 5/1996 | Gevins et al. | 600/544 |
| 7,286,871 | B2 * | 10/2007 | Cohen | 600/544 |
| 7,684,856 | B2 * | 3/2010 | Virtanen et al. | 600/544 |
| 2006/0149139 | A1 * | 7/2006 | Bonmassar et al. | 600/300 |
| 2007/0167858 | A1 * | 7/2007 | Virtanen et al. | 600/544 |
| 2008/0306397 | A1 * | 12/2008 | Bonmassar et al. | 600/544 |
| 2011/0282232 | A1 * | 11/2011 | Pradeep et al. | 600/544 |

OTHER PUBLICATIONS

Allen, Philip J., et al., "A Method for Removing Imaging Artifact from Continuous EEG Recorded during Functional MRI," Academic Press, NeuroImage, vol. 12, pp. 230-239, 2000.

* cited by examiner

*Primary Examiner* — Patricia Mallari
*Assistant Examiner* — Puya Agahi
(74) *Attorney, Agent, or Firm* — Laurence A. Greenberg; Werner H. Stemer; Ralph H. Locher

(57) ABSTRACT

Artifacts are removed from EEG signals by segmenting EEG data that are continuously recorded during an MR scan with respect to a time period based on the MR scan, thereby obtaining n temporally consecutive segments of EEG data. For each segment j of the n segments, it is determined whether movement is detected when the segment j is recorded. In the case of no movement, the segment j is selected for a template k. In case movement is detected, EEG data of segments of the n temporally consecutive segments which have been selected for the template k are averaged, thereby obtaining the template k, the template k is subtracted from the EEG data of the segments, k is incremented, and the segment j is selected for the template k. In case no movement is detected and j=n, the segment j is selected for the template k and EEG data of segments of the n temporally consecutive segments which have been selected for the template k are averaged, thereby obtaining the template k, and the template k is subtracted from the EEG data of the segments.

7 Claims, 2 Drawing Sheets

METHOD AND SYSTEM FOR EEG ARTIFACT CORRECTION IN COMBINED EEG AND FUNCTIONAL MRI RECORDING

BACKGROUND OF THE INVENTION

Field of the Invention

The present invention relates to EEG artifact correction in combined EEG (electroencephalography) and fMRI (functional magnetic resonance imaging) recording. In particular, the present invention relates to a method of removing EEG artifacts induced during an fMRI.

For example, EEG signals are recorded from a patient's head by means of electrodes placed on the patient's head while an fMRI scanner scans slices of the patient's brain. A complete scan of slices is referred to as a volume.

During scanning by the fMRI scanner, artifacts are introduced into the EEG signals, which are caused by alternating electromagnetic fields and high frequency pulses, for example. These pulses are output from the scanner in the same direction. Assuming that the electrodes and cables feeding the EEG signals from the electrodes to an EEG recording apparatus have specific positions at or on the patient's head, the pulses are reproduced as artifacts in the EEG signals continuously in the same manner.

Such uniform artifacts may be removed by segmenting the EEG signals with respect to each volume and averaging the EEG signals corresponding to each of the segmented volumes. That is, EEG data for volumes 1, 2, . . . , n are added and divided by the number of volumes n. In the thus obtained average the EEG signals are minimized while the artifacts remain. Then the average is subtracted from the EEG data of each segment (i.e. volume) so that the artifacts are removed and the EEG signals remain.

Blood pulse artifacts can be removed in a similar manner.

A method of removing repeatedly occurring interferences/artifacts induced by a functional MRI in continuous EEG signals is the so-called average subtraction method described by Allen, Josephs, and Turner: "A Method for Removing Imaging Artifact from Continuous EEG Recorded During Functional MRI," Academic Press, NeuroImage vol. 12, pp. 230-39, 2000.

With the above method it is possible to achieve good results as long as there is no movement of the patient's head wearing the EEG electrodes. In case there is such movement, the topography of the MR and blood pulse artifacts changes, and the results of the above correction method deteriorate.

SUMMARY OF THE INVENTION

It is accordingly an object of the invention to provide a method and a device for artifact correction in combined EEG/fMRI recording which overcome the above-mentioned disadvantages of the heretofore-known devices and methods of this general type and which provides for a method and a system that can dependably remove EEG artifacts induced during fMRI even if there is movement of the patient's head.

With the foregoing and other objects in view there is provided, in accordance with the invention, a method of removing artifacts from EEG signals. The method comprises the following steps:

segmenting EEG data, which is continuously recorded during an MR scan, with respect to a time period based on the MR scan, thereby obtaining n temporally consecutive segments of EEG data, for each segment j of the n segments, determining whether movement is detected when the segment j is recorded, in case no movement is detected, selecting the segment j for a template k, in case movement is detected, averaging EEG data of segments of the n temporally consecutive segments which have been selected for the template k, thereby obtaining the template k, subtracting the template k from the EEG data of the segments, incrementing k, and selecting the segment j for the template k, and in case no movement is detected and j=n, selecting the segment j for the template k and averaging EEG data of segments of the n temporally consecutive segments which have been selected for the template k, thereby obtaining the template k, and subtracting the template k from the EEG data of the segments.

The time period may be a time required for obtaining a volume of MR data in the MR scan.

With the above and other objects in view there is also provided, in accordance with the invention, a system or a device for removing artifacts from EEG signals. The system comprises:

a segmenting and averaging unit configured to segment EEG data, which is continuously recorded during an MR scan, with respect to a time period based on the MR scan, thereby obtaining n temporally consecutive segments of EEG data;

a movement detector configured to detect movement when the EEG data is recorded, and output a movement detection signal to the segmenting and averaging unit; and a subtracting unit, wherein, for each segment j of the n segments, the segmenting and averaging unit is configured to select the segment j for a template k, in case the movement detection signal does not indicate movement for the segment j, in case the movement detection signal indicates movement for the segment j, average EEG data of segments of the n temporally consecutive segments which have been selected for the template k, thereby obtaining the template k, increment k, and select the segment j for the template k; and in case the movement detection signal does not indicate movement for the segment j and j=n, select the segment j for the template k and average EEG data of segments of the n temporally consecutive segments which have been selected for the template k, thereby obtaining the template k;

wherein the subtracting unit is configured to subtract the template k from the EEG data of the segments.

The variables n, j, and k represent integers.

In accordance with a concomitant feature of the invention, the movement is detected by way of an acceleration sensor forming the movement detector.

With the above and other objects in view there is further provided, in accordance with the invention, computer-readable medium having software code portions stored thereon that are configured, when loaded into a computer memory, to carry out the above-summarized EEG data correction method by way of the computer.

Other features which are considered as characteristic for the invention are set forth in the appended claims.

Although the invention is illustrated and described herein as embodied in an EEG artifact correction in combined EEG and functional MRI recording, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 1:
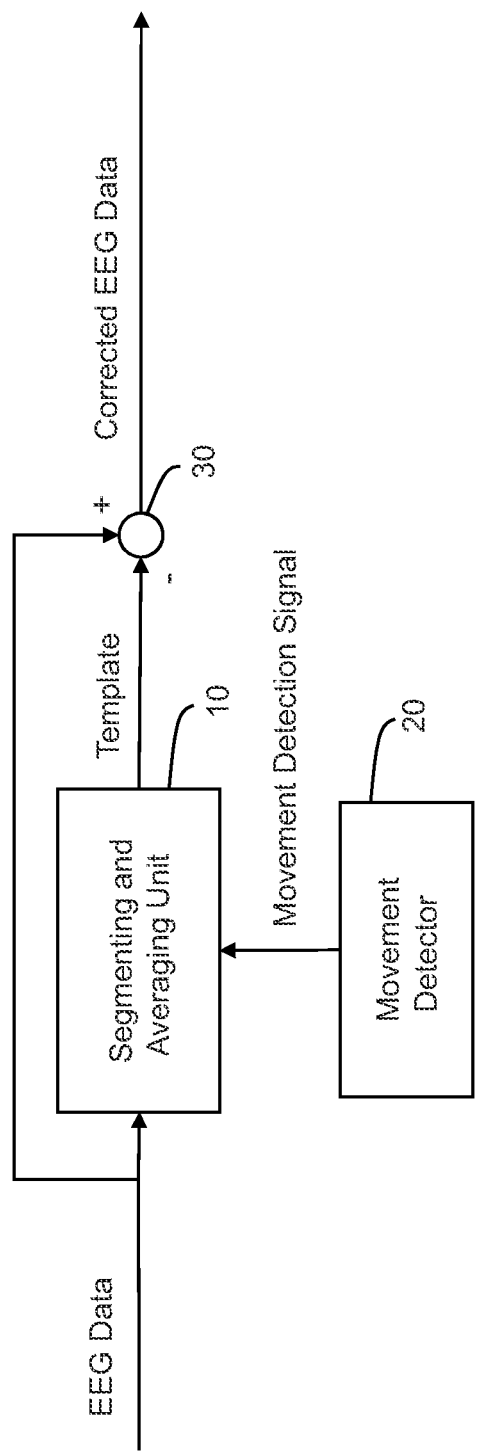
FIG. 1 is a schematic block diagram illustrating a system for removing artifacts from EEG signals according to an exemplary embodiment of the invention.

Referring now to the figures of the drawing in detail and first, particularly, to FIG. 1 thereof, EEG data which are continuously recorded during an MR scan are input to a segmenting and averaging unit 10. A template output from the segmenting and averaging unit 10 is subtracted from the EEG data by a subtracting unit 30 which receives the EEG data and the template as an input and outputs corrected EEG data, i.e. EEG data from which averaged artifacts induced by MR and blood pulses are subtracted. The EEG data are derived from EEG signals fed from EEG electrodes positioned at a patient's head via cables to an analog-digital converter (not shown) which converts the EEG signals to the EEG data. The EEG signals are measured in a combined EEG (electroencephalography) and fMRI (functional magnetic resonance imaging) recording.

A movement detector 20 detects a movement of the patient's head during the recording and outputs a movement detection signal to the segmenting and averaging unit 10. The movement detector 20 may be an acceleration sensor which may be attached to the patient's head. The movement detector 20 may record information about the detected movement. In case the detected movement exceeds a predetermined threshold, the movement detector 20 may indicate this by the movement detection signal output to the segmenting and averaging unit 10. The movement detector 20 may comprise processing resources, memory resources and interfaces for detecting movement and recording information about the detected movement and for outputting the movement detection signal, for example.

Figure 2:
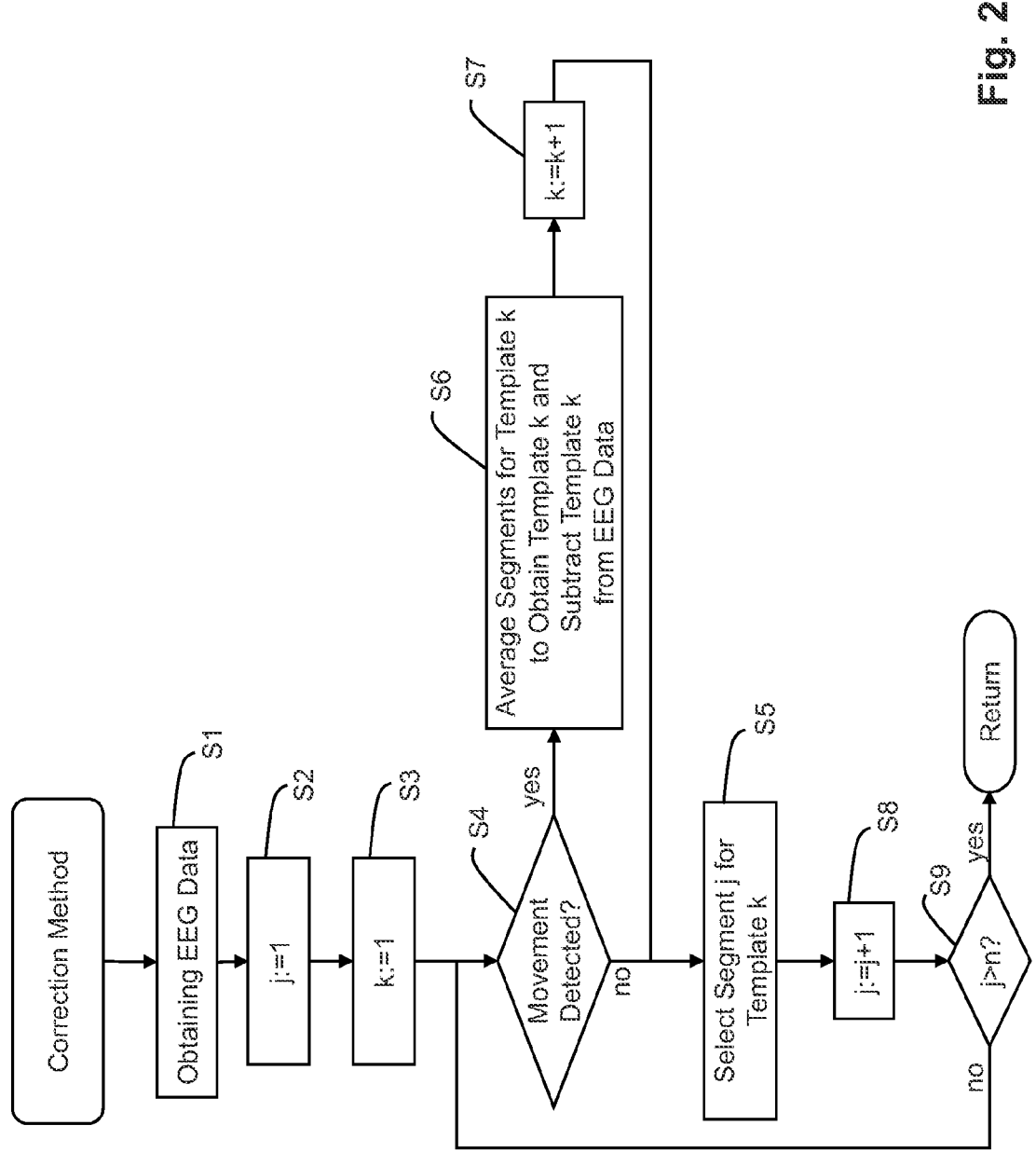
FIG. 2 is a flow chart illustrating a correcting method for removing artifacts from EEG signals according to an exemplary embodiment of the invention.

FIG. 2 shows a flow chart illustrating a correction method according to an embodiment of the invention. In step S1, the EEG data which is continuously recorded during the MR scan as mentioned above is obtained. The EEG data is segmented with respect to a time period based on the MR scan, thereby obtaining n temporally consecutive segments of EEG data. In step S2 a count value of segments is initiated to 1 and in step S3 a count value of templates is initiated to 1.

In step S4 it is determined whether a movement is detected for a segment j. This determination may be made based on the movement detection signal received from the movement detector 20.

In case no movement is detected in step S4, the segment j is selected for a template k in step S5.

Steps S1 to S5 may be executed by the segmenting and averaging unit 10 of FIG. 1.

Otherwise, in case movement is detected in step S4, EEG data of segments of the n temporally consecutive segments which have been selected for the template k is averaged, thereby obtaining the template k, and the template k is subtracted from the EEG data of the segments in step S6. The averaging may be performed by the segmenting and averaging unit 10 shown in FIG. 1, and the subtraction may be executed by the subtracting unit 30.

Thus, corrected EEG data is obtained, i.e. EEG data from which averaged artifacts are subtracted. In step S7, the count value k is incremented. Then the process advances to step S5 in which the segment j is selected for the template k.

In step S8 the count value j is incremented, and in step S9 it is checked whether j exceeds n. If not, the process returns to step S4. If it is determined in step S9 that j exceeds n, the process ends. Steps S7 to S9 may be performed by the segmenting and averaging unit 10.

The segmenting and averaging unit 10 may comprise processing resources, memory resources and interfaces for executing the steps of the method illustrated in FIG. 2 as described above, for receiving the movement detection signal and the EEG data and outputting the template, for example. The segmenting and averaging unit 10 may also receive a signal indicating the time period used for segmenting the EEG data, e.g. from a scanner conducting the MR scan.

It will be understood that also the subtraction in step S6 may be performed by the segmenting and averaging unit 10 including memory resources for buffering the EEG data of the segments for averaging, i.e. the subtracting unit 30 may be part of the segmenting and averaging unit 10. Alternatively or in addition, the subtracting unit 30 may comprise buffers for buffering the EEG data of the segments.

The time period based on the MR scan which is adopted to segment the EEG data may be a time required for obtaining a volume of MR data in the MR scan, i.e. a volume repeat time. However, the time period is not limited thereto and may comprise any repeat time adopted in the MR scan.

For example it is assumed that 100 volumes are obtained during an MR scan. Moreover, it is assumed that the patient's head keeps a first position during recording of volumes 1 to 50, changes to a second position when volume 51 is recorded, and keeps the second position during recording of volumes 52 to 100. With the above-described correction method, two templates for subtraction, generated by averaging, are calculated, a first template for volumes 1 to 50 and a second template for volumes 51 to 100.

Thus, with the above-described correction method, a new template for subtraction can by calculated every time the patient's head moves, and, thus, the MR and blood pulse artifacts can be removed from the EEG data regardless of the movement of the patient's head.

The above-described correction method may be applied online, i.e., during the actual combined EEG and fMRI recording, or offline, i.e. after having recorded the EEG and fMRI data.

Those of skill in the art will readily understand that the above description is illustrative of the invention and it is not to be construed as limiting the invention. Various modifications and applications may become evident to those skilled in the art without departing from the true spirit and scope of the invention as defined by the appended claims.

The invention claimed is:

1. A method of removing artifacts from electroencephalogram (EEG) signals, the method comprises:
   continuously recording EEG data during a magnetic resonance (MR) scan and segmenting the EEG data by a processor with respect to a time period based on the MR scan, to thereby obtain n temporally consecutive segments of EEG data;
   for each segment j of the n segments:

determining whether a movement is detected when the respective segment j is recorded;

if no movement is detected, selecting the segment j for a template k;

if movement is detected, averaging EEG data of segments of the n temporally consecutive segments that have been selected for the template k, thereby modifying, based on data obtained by a movement detector, the template k in which an artifact caused by the movement and detected by the movement detector remained, correcting the artifact by subtracting the average from the EEG data of the segments to minimize the movement artifact in the EEG signals, incrementing k, and selecting the segment j for the template k;

if no movement is detected and j=n, selecting the segment j for the template k and averaging EEG data of segments of the n temporally consecutive segments that have been selected for the template k, thereby modifying, based on the data obtained by said movement detector, the template k in which the artifact caused by the movement and detected by the movement detector remained, and correcting the artifact by subtracting the template k from the EEG data of the segments to minimize the movement artifact in the EEG signals; and outputting a correspondingly corrected EEG data signal.

2. The method according to claim 1, wherein the time period is a time required for obtaining a volume of MR data in the MR scan.

3. The method according to claim 1, which comprises detecting the movement with an acceleration sensor.

4. A system for removing artifacts from electroencephalograph (EEG) signals, the system comprising:

a segmenting and averaging unit configured to segment EEG data that are continuously recorded during a magnetic resonance (MR) scan of a subject, with respect to a time period based on the MR scan, and to thereby obtain n temporally consecutive segments of EEG data;

a movement detector configured to detect movement of the subject when the EEG data are recorded, and connected to output a movement detection signal to said segment and averaging unit; and a subtracting unit, said segmenting and averaging unit being configured, for each segment j of the n segments, to:

select a segment j for a template k, in case the movement detection signal does not indicate movement for the segment j;

in case the movement detection signal indicates movement for the segment j, average EEG data of segments of the n temporally consecutive segments that have been selected for the template k, thereby modifying, based on data obtained by said movement detector, the template k in which an artifact caused by the movement and detected by said movement detector remained, increment k, and select the segment j for the template k;

in case the movement detection signal does not indicate movement for the segment j and j=n, select the segment j for the template k and average EEG data of segments of the n temporally consecutive segments which have been selected for the template k, thereby modifying, based on data obtained by said movement detector, the template k in which an artifact caused by the movement and detected by said movement detector remained; and said subtracting unit being configured to correct the artifact by subtracting the template k from the EEG data of the segments to minimize the movement artifact in the EEG signals.

5. The system according to claim 4, wherein the time period is a time required for obtaining a volume of MR data in the MR scan.

6. The system according to claim 4, wherein said movement detector comprises an acceleration sensor.

7. A non-transitory computer-readable medium having software code portions stored thereon and configured, when loaded into a computer memory, to carry out an electroencephalograph (EEG) data correction method by programming the computer to:

segment EEG data that are continuously recorded during a magnetic resonance (MR) scan, with respect to a time period based on the MR scan, to thereby obtain n temporally consecutive segments of EEG data;

for each segment j of the n segments:

determine whether movement is detected when the segment j is recorded and:

if no movement is detected, select the segment j for a template k;

if movement is detected, average EEG data of segments of the n temporally consecutive segments that have been selected for the template k, thereby modifying, based on the data obtained by the movement by a movement detector, the template k in which an artifact caused by the movement and detected by the movement detector remained, correct the artifact by subtracting the average from the EEG data of the segments to minimize the movement artifact in the EEG signals, increment k, and select the segment j for the template k; and if movement is detected and j=n, select the segment j for the template k and average EEG data of segments of the n temporally consecutive segments that have been selected for the template k, to thereby modify, based on the data obtained by the movement detector, the template k in which an artifact caused by the movement and detected by the movement detector remained, and correct the artifact by subtracting the average from the EEG data of the segments to minimize the movement artifact in the EEG signals.

* * * * *